(12) United States Patent
Kan et al.

(10) Patent No.: US 10,881,384 B2
(45) Date of Patent: Jan. 5, 2021

(54) METHOD OF ATTACHING A MESH TO A COATED LOOP MEMBER OF A SURGICAL SNARE DEVICE

(71) Applicant: EndoChoice, Inc., Alpharetta, GA (US)

(72) Inventors: Gil Kan, Alpharetta, GA (US); Tracey Knapp, Snellville, GA (US); Charlie Jacobs, Loganville, GA (US)

(73) Assignee: EndoChoice, Inc., Alpharetta, GA (US)

( * ) Notice: Subject to any disclaimer, the term of this patent is extended or adjusted under 35 U.S.C. 154(b) by 575 days.

(21) Appl. No.: 15/331,505

(22) Filed: Oct. 21, 2016

(65) Prior Publication Data

US 2017/0035403 A1    Feb. 9, 2017

Related U.S. Application Data

(63) Continuation-in-part of application No. 14/858,622, filed on Sep. 18, 2015, now Pat. No. 10,149,691.

(60) Provisional application No. 62/245,319, filed on Oct. 23, 2015, provisional application No. 62/162,786, (Continued)

(51) Int. Cl.
*A61B 17/00* (2006.01)
*A61B 17/221* (2006.01)
*A61B 17/50* (2006.01)
*A61B 17/22* (2006.01)

(52) U.S. Cl.
CPC ...... *A61B 17/00234* (2013.01); *A61B 17/221* (2013.01); *A61B 17/50* (2013.01); *A61B 2017/00287* (2013.01); *A61B 2017/00526* (2013.01); *A61B 2017/2212* (2013.01); *A61B 2017/22035* (2013.01)

(58) Field of Classification Search
CPC ........ A61B 2017/22035; A61B 17/221; A61B 17/32056; A61B 17/00234; A61B 2017/00358; A61B 2017/00292; A61B 2017/00287; A61B 17/22031
See application file for complete search history.

(56) References Cited

U.S. PATENT DOCUMENTS 3,124,136 A * 3/1964 Usher .................. A61L 31/048
                                               606/213
5,486,182 A   1/1996 Nakao et al.
(Continued)

FOREIGN PATENT DOCUMENTS

WO    WO 99/53851 A1    10/1999
WO    WO 2016/044729 A1    3/2016

*Primary Examiner* — Shaun L David
*Assistant Examiner* — Christina C Lauer
(74) *Attorney, Agent, or Firm* — Bookoff McAndrews, PLLC

(57) ABSTRACT

This specification describes methods of attaching a mesh to a loop member, which includes covering a wire with a layer, manipulating the wire along with the layer to form the loop member, placing the mesh over the loop member, transferring heat to the layer to cause it to partially melt and become tacky, allowing the mesh to fuse with the tacky layer and form a secure bond on cooling, and trimming portions of the mesh extending beyond the circumference of the loop member. A retrieval device formed by the methods include the loop member and attached mesh positioned, and longitudinally movable within, a tubular sheath. The loop member and mesh are deployed to capture a target object and partially retracted for removal of the object.

19 Claims, 15 Drawing Sheets

Related U.S. Application Data filed on May 17, 2015, provisional application No. 62/052,538, filed on Sep. 19, 2014.

(56) References Cited

U.S. PATENT DOCUMENTS

| | | | |
|---|---|---|---|
| 5,782,840 A * | 7/1998 | Nakao | A61B 18/14 606/110 |
| 2004/0193207 A1 | 9/2004 | Boismier | |
| 2004/0267306 A1 | 12/2004 | Blaeser et al. | |
| 2005/0101987 A1 | 5/2005 | Salahieh | |
| 2007/0129719 A1 * | 6/2007 | Kendale | A61B 1/00096 606/41 |
| 2009/0312745 A1 * | 12/2009 | Goldfarb | A61M 25/0041 604/514 |
| 2012/0046667 A1 | 2/2012 | Cherry et al. | |
| 2013/0245624 A1 * | 9/2013 | Bahney | A61B 17/32056 606/47 |
| 2014/0194911 A1 | 7/2014 | Johnson et al. | |
| 2015/0327878 A1 | 11/2015 | Chu et al. | |

\* cited by examiner

METHOD OF ATTACHING A MESH TO A COATED LOOP MEMBER OF A SURGICAL SNARE DEVICE

CROSS-REFERENCE TO RELATED APPLICATIONS

The present application relies on, for priority, U.S. Patent Provisional Application No. 62/245,319, entitled "Method of Attaching a Mesh to a Coated Loop Member of a Surgical Snare Device" and filed on Oct. 23, 2015.

The present application is a continuation-in-part application to U.S. patent application Ser. No. 14/858,622 (Publication No. 20160081702), entitled "Method of Attaching A Mesh to A Coated Loop Member of a Surgical Snare Device", and filed on Sep. 18, 2015, which relies on, for priority, both U.S. Patent Provisional Application No. 62/052,538, entitled "Method of Attaching a Mesh to a Coated Loop Member of a Surgical Snare Device" and filed on Sep. 19, 2014, and U.S. Patent Provisional Application No. 62/162,786, entitled "Method of Attaching a Mesh to a Coated Loop Member of a Surgical Snare Device" and filed on May 17, 2015.

The above-mentioned applications are herein incorporated by reference in their entirety.

FIELD

The present specification relates generally to surgical instruments. More particularly, the present specification relates to a surgical snare device used to remove objects from a body lumen wherein a mesh or net is fused and bonded with a coated loop member of the surgical snare device.

BACKGROUND

Existing surgical devices for grasping and removing foreign objects from body organs or cavities include mechanically actuated forceps, mechanically actuated snares or mechanically actuated baskets. Each of these surgical devices may be positioned within the body under endoscopic, fluoroscopic or direct visualization.

Mechanically actuated snares include an assembly of a flexible web member mounted on a loop of wire enclosed within a sheath. The loop of wire can be extended beyond the sheath to automatically expand into a shaped opening and, as a result, also open the attached/mounted web member into a capture pocket. The size of the opening is controlled by the length of wire advanced beyond the end of the sheath. In use, after the snare is positioned adjacent an object, the wire is advanced beyond the end of the sheath until a loop larger than the object is formed. The loop is then positioned until the web member and a plane of the loop encompass the object. The sheath is then advanced and the wire retracted so that the loop and the web member close around and ensnare/trap the object.

The web member is typically attached to the loop of wire through weaving and/or by using clips or ringlets along a circumference of the loop of wire. When the loop is withdrawn into the sheath, to close the loop around an object, the strands of material connecting the web member to the loop and in some instances the material comprising the web member may slide along the loop and became concentrated at a distal end of the loop. The web material may also bunch together and become interposed between the object and the distal end of the loop. Similarly, the presence of clips or ringlets by which the web member is joined to the loop may also interfere with and make more difficult and time consuming the capturing of the object.

There is thus a need in the art for an improved method of attaching or connecting a web member, mesh or net to a loop member of a surgical snare device, such that it does not interfere with the procedure.

SUMMARY

The following embodiments and aspects thereof are described and illustrated in conjunction with systems, tools and methods, which are meant to be exemplary and illustrative, and not limiting in scope. The present application discloses numerous embodiments.

The present specification discloses a method of attaching a mesh to a loop member, the method comprising the steps of: manipulating a wire to form a loop member having a shape, wherein the wire is of a first material; applying a layer of adhesive to the loop member; placing the mesh over the loop member, wherein the mesh is of a second material, wherein the mesh at least partially covers a circumference of the loop member and wherein portions of the mesh extend beyond a circumference of the loop member; exposing the adhesive to an energy source while the mesh is positioned over the loop member; allowing the mesh to bond with said adhesive; and trimming said portions of the mesh extending beyond the circumference of the loop member, wherein the loop member along with the attached mesh is configured to be collapsible by retracting the loop member and attached mesh into a lumen of a sheath and expandable to said shape by extending the loop member and attached mesh out of said sheath.

The energy source may be at least one of a heat radiating oven, an ultraviolet radiation source, an infrared radiation source, and a laser source.

The shape of said loop member may be any one of oval, circular, tear drop, square, rectangular, quadrilateral, or polygonal.

Optionally, the loop member has a first dimension along a longitudinal axis passing through a center of the loop member and a second dimension along another axis perpendicular to the longitudinal axis and also passing through the center of the loop member. The first dimension may be longer than said second dimension. The first dimension may range from 30 to 70 millimeters and the second dimension may range from 15 to 40 millimeters. The first dimension may be equal to said second dimension. The first dimension may be less than said second dimension.

The first material of said wire may be at least one of Nitinol, steel or stainless steel.

Optionally, said mesh, after bonding, has a pouch at a center of the loop member.

The present specification also discloses a method of attaching a mesh to a loop member, the method comprising the steps of: coating a wire of a first material with a layer of a second material; manipulating the wire and the layer to form the loop member, wherein the loop member has a shape and wherein the loop member has a first dimension along a longitudinal axis passing through a center of the loop member and a second dimension along another axis perpendicular to the longitudinal axis and also passing through the center of the loop member; placing the mesh over the loop member, wherein the mesh is of a third material, wherein the mesh at least partially covers a circumference of the loop member and wherein portions of the mesh extend beyond a circumference of the loop member; transferring heat to the layer to cause the second material to partially melt and have increased tackiness while the mesh is positioned over the loop member; allowing the mesh to bond together with said second material of said layer along a circumference of said loop member and form a secure bond on cooling; and trimming said portions of the mesh extending beyond the circumference of the loop member, wherein the loop member along with the attached mesh is configured to be collapsible by retracting the loop member along with the attached mesh into a lumen of a sheath and to be expandable to said shape by extending the loop member along with the attached mesh out of said sheath.

The shape of the loop member may be any one of oval, circular, tear drop, square, rectangular, quadrilateral, and polygonal.

The first dimension may be longer than said second dimension. The first dimension may range from 30 to 70 millimeters and the second dimension may range from 15 to 40 millimeters. The first dimension may be equal to said second dimension. The first dimension may be less than said second dimension.

The first material of said wire may be at least one of Nitinol, steel or stainless steel.

The third material of said mesh may be at least one of Nylon or PET.

Optionally, said loop member is heated by exposing said loop member to hot air, wherein said hot air has a temperature within a range of 120 to 180° C. or a temperature within a range of the melting temperature of the second material.

Optionally, said mesh, after bonding, has a pouch at the center of the loop member.

The present specification also discloses a retrieval device comprising: a flexible wire loop; a bonding material layered over said wire loop; a mesh bonded to said bonding material configured to form a net having an opening circumscribed by said wire loop, wherein said mesh has been fixedly bonded to said bonding material through a process of heating said bonding material to a tacky state, placing an outer edge of said mesh over said bonding material, and allowing said bonding material to cool; and a tubular sheath comprising an elongate body, a proximal end, a distal end, and a lumen within, wherein said flexible wire loop with bonded mesh is adapted to be retractable into said lumen and adapted to be extendable out of said lumen through an opening at said distal end of said tubular sheath by manipulation of a link member positioned at said proximal end of said tubular sheath and wherein at least one of said loop and said mesh comprise a color such then when exposed to light in a first wavelength range, reflects light having a wavelength range of 400 nm to 570 nm and 620 nm to 750 nm and absorbs light having a wavelength range of 571 nm to 619 nm.

Optionally, said mesh comprises a plurality of pores.

The pores may have a hexagonal, circular, triangular, square, rectangular, pentagonal or multi-sided polygonal shape.

The present specification also discloses a method of attaching a mesh to a loop member, the method comprising the steps of: manipulating a wire to form a loop member having a shape, wherein the wire is of a first material; applying a layer of adhesive to the loop member; placing the mesh over the loop member, wherein the mesh is of a second material, wherein the mesh at least partially covers a circumference of the loop member and wherein portions of the mesh extend beyond a circumference of the loop member; exposing the adhesive to ultraviolet radiation while the mesh is held over the loop member; allowing the mesh to bond with said adhesive; and trimming said portions of the mesh extending beyond the circumference of the loop member, wherein the loop member along with the attached mesh is collapsible by retracting into a lumen of a sheath and expandable to said shape when extended out of said sheath.

The shape of said loop member may be any one of oval, circular, tear drop, square, rectangular, quadrilateral, or polygonal.

The loop member may have a first dimension along a longitudinal axis passing through a center of the loop member and a second dimension along another axis perpendicular to the longitudinal axis and also passing through the center of the loop member. The first dimension may be longer than said second dimension. Optionally, said first dimension ranges from 30 to 70 millimeters and said second dimension ranges from 15 to 40 millimeters. Alternatively, said first dimension is equal to said second dimension. Still alternatively, first dimension is less than said second dimension.

The first material of said wire may be at least one of Nitinol, steel or stainless steel.

The second material of said mesh may be polymeric. Optionally, the second material of said mesh is at least one of Nylon, PET or Pebax.

The mesh, after bonding, may have a pouch at a center of the loop member.

The present specification also discloses a retrieval device comprising: a flexible wire loop; a bonding material layered over said wire loop; a mesh bonded to said bonding material to create a net having an opening circumscribed by said wire loop, wherein said mesh has been fixedly bonded to said bonding material through a process of heating said bonding material to a slightly sticky, partially wet, or tacky state, placing an outer edge of said mesh over said bonding material, and allowing said bonding material to cool; and a tubular sheath comprising an elongate body, a proximal end, a distal end, and a lumen within, wherein said flexible wire loop with bonded mesh is retractable into said lumen and extendable out of said lumen through an opening at said distal end of said tubular sheath by manipulation of a transmission link positioned at said proximal end of said tubular sheath.

In some embodiments, the mesh comprises a plurality of pores. Optionally, said pores have a hexagonal, circular, triangular, square, rectangular, pentagonal or multi-sided polygonal shape.

Optionally, the layer and/or said mesh comprise a color such then when exposed to light in a first wavelength range, reflects light in a second wavelength range. Still optionally, the first wavelength range is 400 to 750 nm. Still optionally, the second wavelength range is 380 to 750 nm. Still optionally, wavelengths in the range of 571 to 619 nm are excluded from said second wavelength range.

The present specification also discloses a method of attaching a mesh to a loop member, the method comprising the steps of: coating a wire of a first material with a layer of a second material; manipulating the wire and the layer to form the loop member, wherein the loop member has a shape and wherein the loop member has a first dimension along a longitudinal axis passing through a center of the loop member and a second dimension along another axis perpendicular to the longitudinal axis and also passing through the center of the loop member; placing the mesh over the loop member, wherein the mesh is of a third material, wherein the mesh at least partially covers a circumference of the loop member and wherein portions of the mesh extend beyond a circumference of the loop member; transferring heat to the layer to cause the second material to partially melt and become tacky, slightly sticky, or partially wet while the mesh is held over the loop member; allowing the mesh to bond together with said partially melted and tacky second material of said layer along a circumference of said loop member and form a secure bond on cooling; and trimming said portions of the mesh extending beyond the circumference of the loop member, wherein the loop member along with the attached mesh is configured to be collapsible by retracting into a lumen of a sheath and expandable to said shape when extended out of said sheath.

The shape of the loop member may be any one of oval, circular, tear drop, square, rectangular, quadrilateral, and polygonal.

Optionally, said first dimension is longer than said second dimension. Still optionally, said first dimension ranges from 30 to 70 millimeters and said second dimension ranges from 15 to 40 millimeters. Alternatively, said first dimension is equal to said second dimension. Still alternatively, said first dimension is less than said second dimension.

The first material of said wire may be at least one of Nitinol, steel or stainless steel. Optionally, the second material of said layer is polymeric. Still optionally, the second material of said layer is at least one of: Nylon, Pebax or PET.

Optionally, the third material of said mesh is polymeric. Still optionally, the third material of said mesh is at least one of Nylon or PET.

The layer may be coated over said wire.

Optionally, said layer comprises a hollow tube into which said wire is inserted.

Optionally, said mesh has a shape approximating said shape of said loop member.

The heat may be transferred to said second material of said layer by heating said wire. The wire may be heated electrically using an external electrical source. The heat may be transferred to said second material of said layer by heating said loop member while said mesh is held over said loop member. Optionally, said loop member is heated by exposing said loop member to hot air, wherein said hot air has a temperature within a range of 120 to 180° C. or within a range of the melting temperature of the second material.

Optionally, said layer has a thickness ranging from 0.05 mm to 0.6 mm.

The mesh, after bonding, may have a pouch at the center of the loop member.

The present specification also discloses a method of attaching a mesh to a loop member, the method comprising the steps of: manipulating a wire to form a shaped wire, wherein the wire is of a first material; covering the shaped wire with a layer of a second material to form the loop member; placing the mesh over the loop member, wherein the mesh is of a third material, wherein the mesh at least partially covers a circumference of the loop member and wherein portions of the mesh extend beyond a circumference of the loop member; transferring heat to the layer to cause the second material to partially melt and become tacky, slightly sticky, or partially wet while the mesh is held over the loop member; allowing the mesh to bond with said partially melted and tacky second material of said layer; and trimming said portions of the mesh extending beyond the circumference of the loop member, wherein the loop member along with the attached mesh is collapsible by retracting into a lumen of a sheath and expandable to said shape when extended out of said sheath.

The shape of said wire may be any one of oval, circular, tear drop, square, rectangular, quadrilateral, or polygonal.

The loop member may have a first dimension along a longitudinal axis passing through a center of the loop member and a second dimension along another axis perpendicular to the longitudinal axis and also passing through the center of the loop member. The first dimension may be longer than said second dimension. Optionally, said first dimension ranges from 30 to 70 millimeters and said second dimension ranges from 15 to 40 millimeters. Alternatively, said first dimension is equal to said second dimension. Still alternatively, said first dimension is less than said second dimension.

The first material of said wire may be at least one of Nitinol, steel or stainless steel.

The second material of said layer may be polymeric. Optionally, the second material of said layer is at least one of Nylon, PET or Pebax.

The third material of said mesh may be polymeric. Optionally, the third material of said mesh is at least one of Nylon or PET.

The layer may be coated over said shaped wire.

Optionally, said layer is a hollow tube into which said shaped wire is inserted.

Heat may be transferred to said second material of said layer by heating said shaped wire. Optionally, said shaped wire is heated electrically using an external electrical source.

Heat may be transferred to said second material of said layer by heating said loop member while said mesh is held over said loop member. Optionally, said loop member is heated by exposing said loop member to a blast of hot air, wherein said hot air has a temperature within a range of 120 to 180° C. or within a range of the melting temperature of the second material.

Optionally, said layer has a thickness ranging from 0.05 mm to 0.6 mm.

The mesh, after bonding, may have a pouch at a center of the loop member.

The present specification also discloses a method of attaching a mesh to a loop member, the method comprising the steps of: covering a wire of a first material with a layer of a second material; manipulating the wire along with the layer to form the loop member, wherein the loop member has a shape and wherein the loop member has a first dimension along a longitudinal axis passing through a center of the loop member and a second dimension along another axis perpendicular to the longitudinal axis and also passing through the center of the loop member; placing the loop member on a base fixture to be held, at least in part, by a plurality of magnets embedded within the base fixture, wherein the held loop member circumscribes a hollow portion formed within the base fixture, said hollow portion configured to receive a pouch form fixture; placing the mesh over the loop member, wherein the mesh is of a third material, wherein the mesh at least partially covers a circumference of the loop member along with the hollow portion and wherein portions of the mesh extend beyond a circumference of the loop member; placing the pouch form fixture over the mesh thereby pressing the mesh into the hollow portion; transferring heat to the layer to cause the second material to partially melt and become tacky, slightly sticky, or partially wet while the mesh is held over the loop member; allowing the mesh to fuse with said partially melted second material of said layer along a circumference of said loop member and form a secure bond on cooling; and trimming said portions of the mesh extending beyond the circumference of the loop member, wherein the loop member along with the attached mesh is collapsible by retracting into a lumen of a sheath and expandable to said shape when extended out of said sheath.

The shape of the loop member may be any one of oval, circular, tear drop, square, rectangular, quadrilateral, and polygonal.

The first dimension may be longer than said second dimension. Optionally, said first dimension ranges from 30 to 70 millimeters and said second dimension ranges from 15 to 40 millimeters. Alternatively, said first dimension is equal to said second dimension. Still alternatively, said first dimension is less than said second dimension.

The first material of said wire may be Nitinol, steel or stainless steel.

The second material of said layer may be polymeric. Optionally, the second material of said layer is Nylon, Pebax or PET.

The third material of said mesh may be polymeric. Optionally, the third material of said mesh is Nylon or PET.

The layer may be coated over said wire.

Optionally, said layer is a hollow tube into which said wire is inserted.

The mesh may have a shape approximating said shape of said loop member.

Heat may be transferred to said second material of said layer by heating said wire. Optionally, said wire is heated electrically using an external electrical source.

Optionally, heat is transferred to said second material of said layer by heating said loop member while said mesh is held over said loop member. Optionally, said loop member is heated by exposing said loop member to a blast of hot air, wherein said hot air has a temperature within a range of 120 to 180° C. or within a range of the melting temperature of the second material.

Optionally, said layer has a thickness ranging from 0.05 mm to 0.6 mm.

The mesh, after bonding, may have a pouch at the center of the loop member.

The present specification also discloses a method of attaching a mesh to a loop member, the method comprising the steps of: manipulating a wire to form a shaped wire, wherein the wire is of a first material; covering the shaped wire with a layer of a second material to form the loop member; placing the loop member on a base fixture to be held, at least in part, by a plurality of magnets embedded within the base fixture, wherein the held loop member encloses, there between, a hollow portion formed within the base fixture, said hollow portion configured to receive a pouch form fixture; placing the mesh over the loop member, wherein the mesh is of a third material, wherein the mesh at least partially covers a circumference of the loop member along with the hollow portion and wherein portions of the mesh extend beyond a circumference of the loop member; placing the pouch form fixture over the mesh to press the mesh into the hollow portion; transferring heat to the layer to cause the second material to partially melt and become tacky, slightly sticky, or partially wet while the mesh is held over the loop member; allowing the mesh to bond with said partially melted second material of said layer; and trimming said portions of the mesh extending beyond the circumference of the loop member, wherein the loop member along with the attached mesh is collapsible by retracting into a lumen of a sheath and expandable to said shape when extended out of said sheath.

The aforementioned and other embodiments of the present specification shall be described in greater depth in the drawings and detailed description provided below.

BRIEF DESCRIPTION OF THE DRAWINGS

These and other features and advantages of the present invention will be further appreciated, as they become better understood by reference to the following detailed description when considered in connection with the accompanying drawings.

DETAILED DESCRIPTION

A surgical snare or retrieval device for retrieving an object from within a human subject is disclosed. The snare device is designed for use within an endoscope and may be used for retrieving relatively heavy objects within relatively tight lumens, such as for example, an impacted food bolus from the esophagus. In discussing the device, the terms distal and proximal are used with respect to an operator's hand. In other words, when the device is used within a working/service channel of an endoscope or similar device, the proximal and distal orientations are relative to the surgeon or operator of the device, wherein a proximal position represents a portion of the device close to the surgeon or operator of the device and a distal position represents the far tip of the device that is directed toward the patient.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

It should be noted herein that any feature or component described in association with a specific embodiment may be used and implemented with any other embodiment unless clearly indicated otherwise.

In the description and claims of the application, each of the words "comprise" "include" and "have", and forms thereof, are not necessarily limited to members in a list with which the words may be associated.

As used herein, the indefinite articles "a" and "an" mean "at least one" or "one or more" unless the context clearly dictates otherwise.

It is noted that the term "endoscope" as mentioned to herein may refer particularly to a colonoscope and a gastroscope according to some embodiments, but is not limited only to colonoscopes and gastroscopes. The term "endoscope" may refer to any instrument used to examine the interior of a hollow organ or cavity of the body.

Figure 1A:
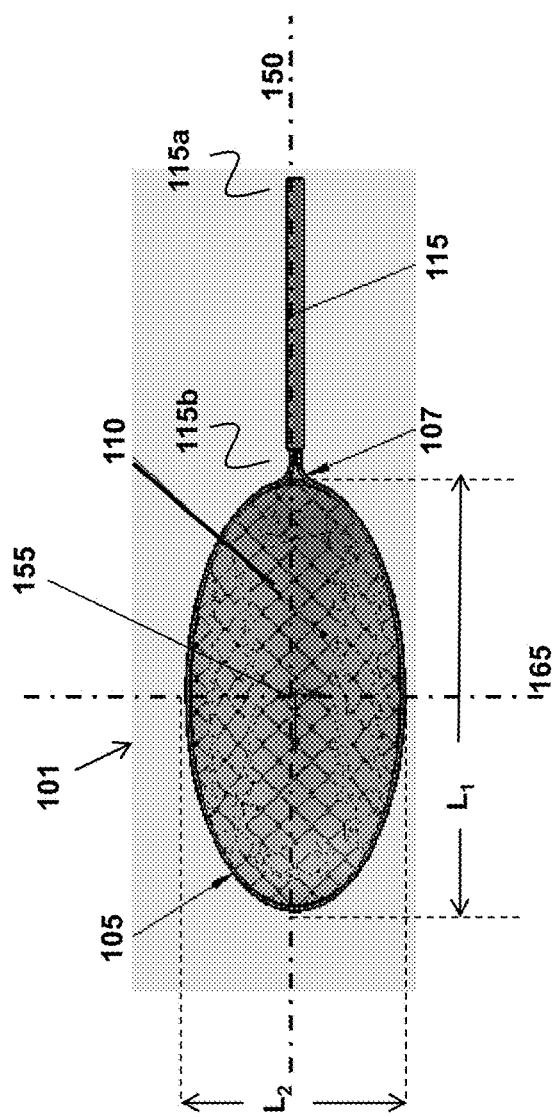
FIG. 1A is a bottom perspective view of a snare loop in accordance with an embodiment of the present specification.
Figure 1B:
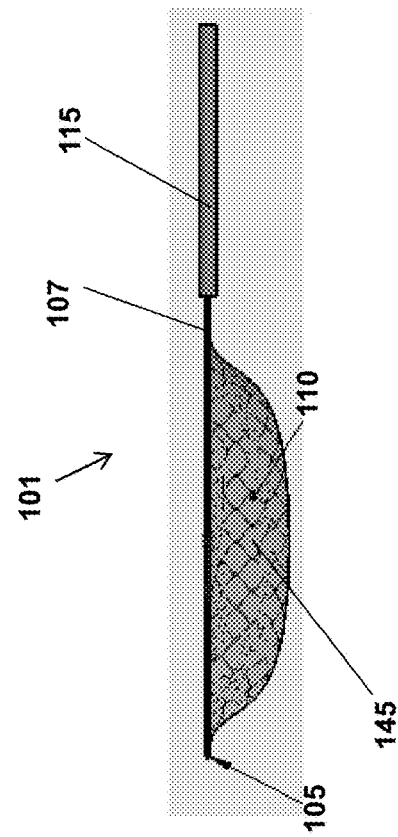
FIG. 1B is a side perspective view of the snare loop of FIG. 1A.
Figure 2A:
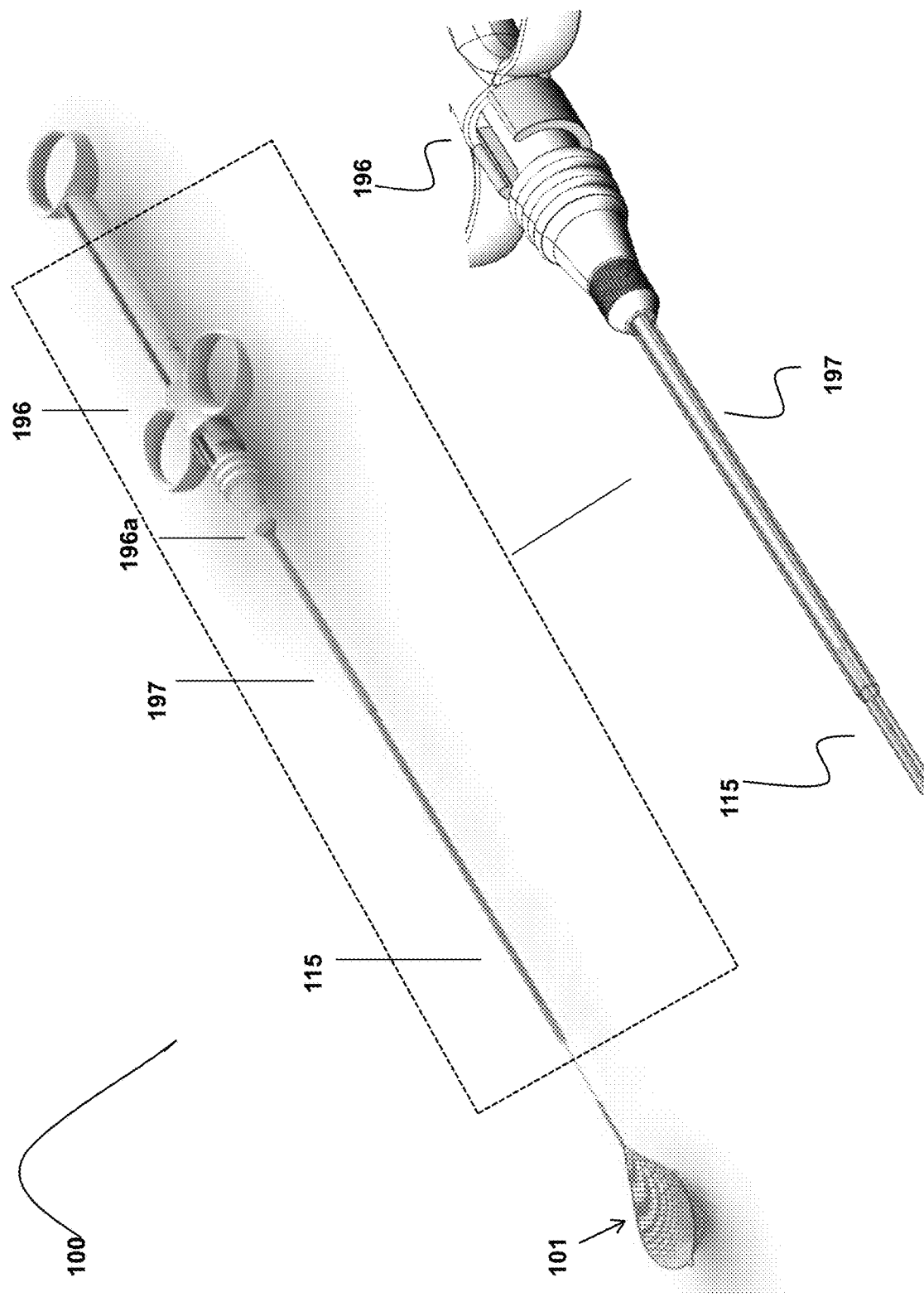
FIG. 2A is a perspective view of a target object capture and retrieval snare device in accordance with an embodiment, also showing an enlarged portion.
Figure 3:
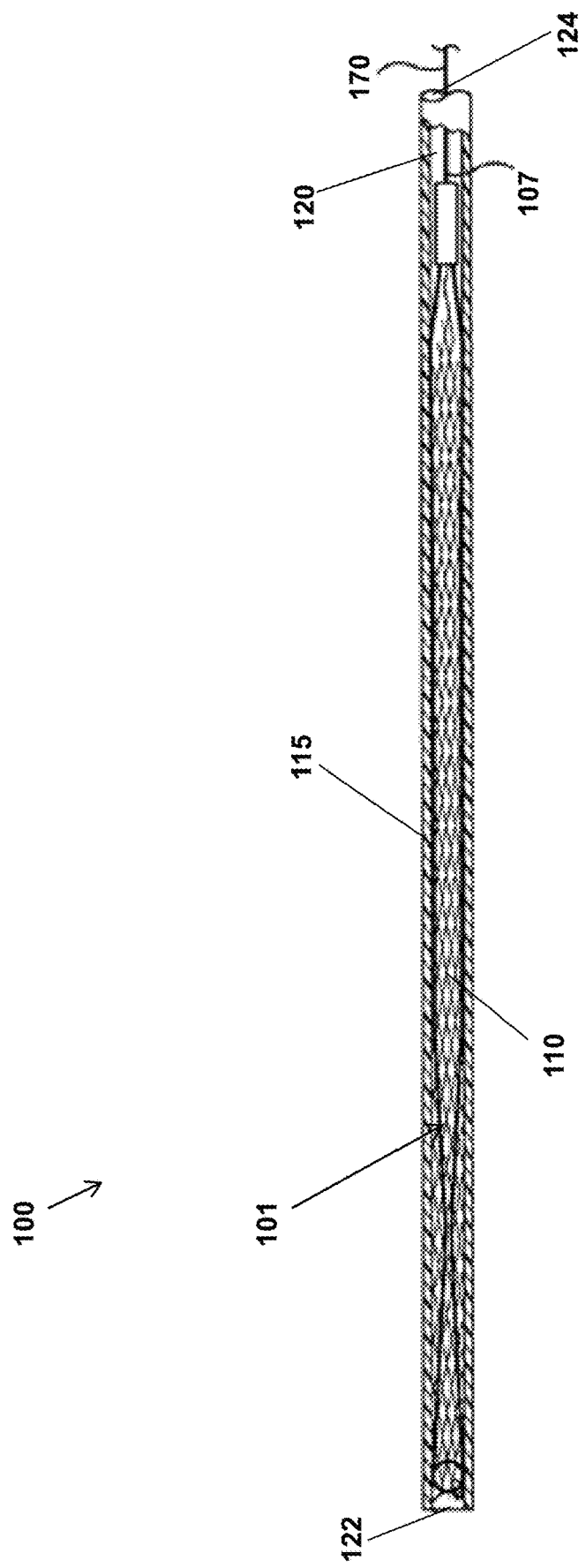
FIG. 3 is a cross-section view of a tubular member or sheath, within which the snare loop of FIG. 1A is stored and in a fully retracted or collapsed position.

FIGS. 1A and 1B are, respectively, bottom and side perspective views of a snare loop 101, while FIGS. 2A and 3 are, respectively, perspective and longitudinal cross-section views of a target object capture and retrieval snare device 100 in accordance with an embodiment of the present specification. Referring now to FIGS. 1A, 1B, 2A and 3, the snare loop 101 comprises a flexible and extensible coated loop member 105 (hereinafter interchangeably also referred to as a "loop") to which a mesh or net 110 is severably, removably, but securely attached or connected. The loop member 105 is described as "coated" because the wire of the loop 105 is coated or enveloped by a bonding material, as discussed below with reference to FIG. 3. The snare device 100 further comprises a tubular member or sheath 115 having an elongate body with a proximal end 115a and a distal end 115b, and a passage or lumen 120 within for retrievably storing, therein, the coated loop member 105 with the attached mesh or net 110 when in a fully collapsed and retracted position, as depicted in FIG. 3.

Figure 2B:
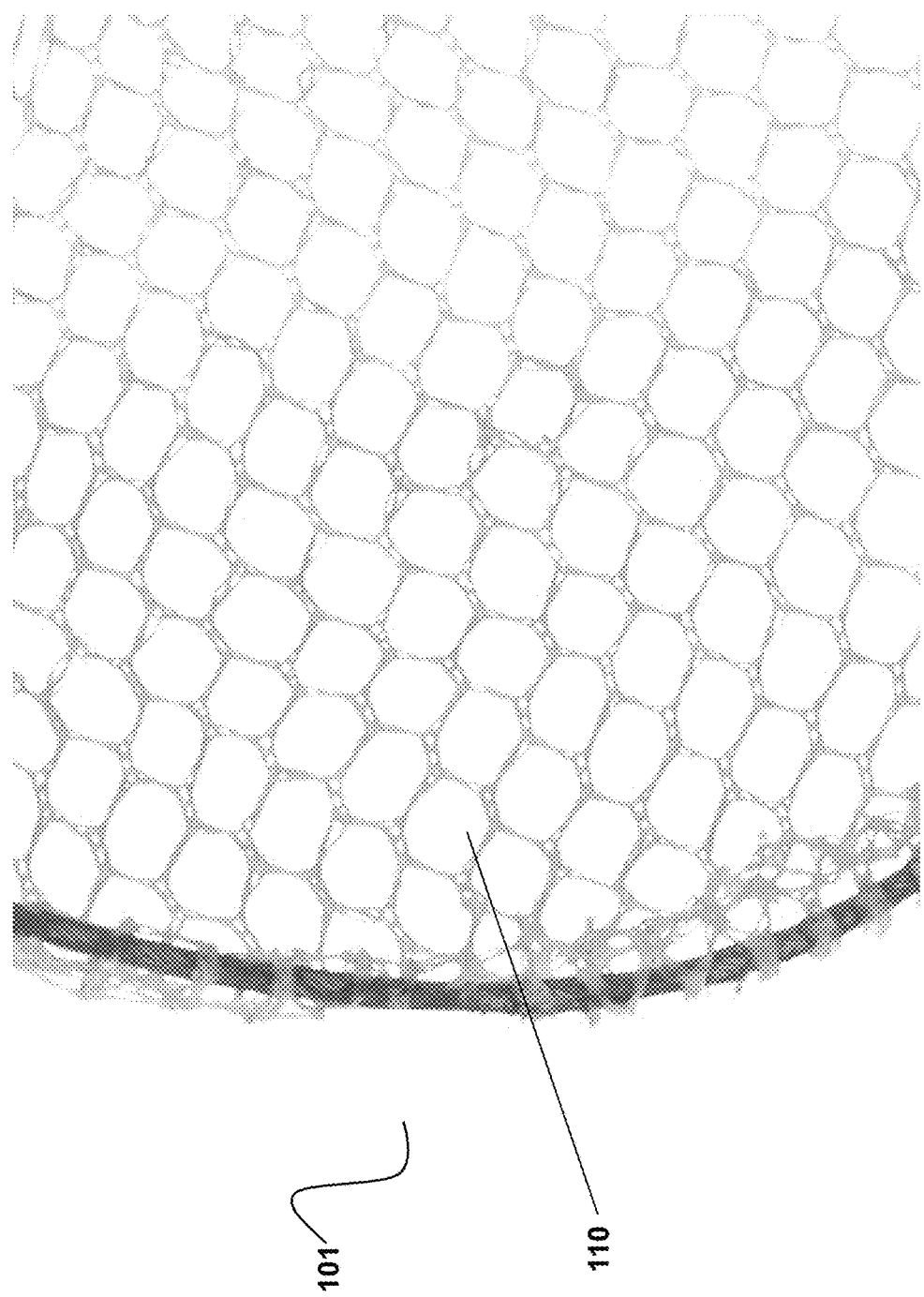
FIG. 2B is an enlarged, perspective view of a portion of a snare loop having a porous mesh in accordance with an embodiment of the present specification.

In one embodiment, the mesh or net 110 is formed by a process such as, but not limited to, wrap knitting a plurality of strands of a polymeric material such as Nylon or PET (Polyethylene Terephthalate) (or other polymers described later in this specification) while the tubular member or sheath 115 is fabricated from an insulating flexible material including high density polyethylene (HDPE), tetrafluoroethylene (TFE) resins or polytetrafluoroethylene (PTFE) polymers, such as Teflon® and Fluon®. In accordance with an embodiment, the polymeric material of the mesh, net or web 110 has elastomeric properties such that the polymeric material may be advanced, stretched or elongated by a minimum of 10% to 40% in a machine direction (MD) and advanced, stretched or elongated by a minimum of 20% to 70% in a cross machine direction (CMD). Persons of ordinary skill in the art would appreciate that the term "machine direction" (MD) is used herein to refer to the direction of material flow through a process while the term "cross-machine direction" (CMD) is used herein to refer to a direction that is generally perpendicular to the machine direction. In various embodiments, the mesh 110 has a porosity ranging between 15 and 40 holes per cm$^2$. In some embodiments, the thickness of the polymeric material forming the mesh or net 110 ranges between 0.05 mm and 0.3 mm. Alternatively, the mesh 110 may be a continuous membrane or web of a polymeric material. Also, in various embodiments, the mesh, net or web 110 is textured or non-textured. In accordance with an embodiment, the mesh, net or web 110 comprises a pouch or sag 145 upon bonding the mesh 110 with the coated loop member 105. FIG. 2B is an enlarged, perspective view of a portion of the snare loop 101 including a mesh 110 which comprises a plurality of 'shaped' pores in accordance with various embodiments. In one embodiment, as shown in FIG. 2B, each of the plurality of pores of the mesh 110 are shaped in the form of a six sided polygon or a hexagon. In various alternate embodiments, each of the plurality of pores may have shapes such as, but not limited to, circular, triangular, square, rectangular, pentagon or any other multi-sided polygon shape.

The sheath 115 has a distal opening 122, in communication with its lumen 120, through which the coated loop member 105 can be partially or fully extended for deployment and can be partially or fully retracted for storage. The extension and retraction of the coated loop member 105, from within the sheath lumen 120, is effectuated, in one embodiment, using a motion transmission link 170 that connects to a proximal end 107 of the coated loop member 105 through a proximal opening 124 of the sheath 115. In various embodiments, the motion transmission link 170 is a hollow tube, a twisted strand wire or a braided wire of suitable rigid material, such as stainless steel. When an operator pulls the link 170 out from the proximal opening 124, the coated loop member 105 is retracted into the sheath 115, whereas when the operator pushes the link 170 into the proximal opening 124, the coated loop member 105 extends out beyond the distal opening 122 of the sheath 115.

As shown in FIG. 2A, the sheath 115 extends distally from a distal end 196a of a handle assembly 196. In one embodiment, a length of the sheath 115 proximate the distal end 196a of the handle assembly 196 includes a shaft strain relief 197. The shaft strain relief 197 overlays sheath 115 and provides strain relief to the rigid motion transmission link 170 (shown in FIG. 3) as the transmission link 170 is advanced into the sheath 115 to deploy the snare loop. The shaft strain relief 197 ensures smooth movement of the transmission link 170 to facilitate proper deployment of the snare loop.

Figure 4:
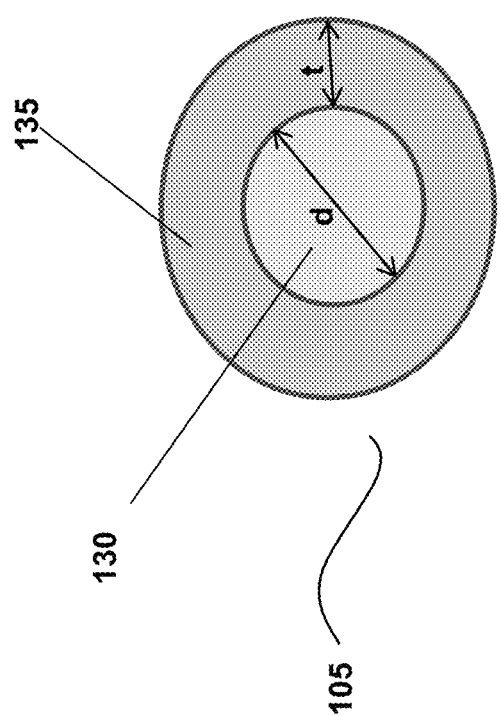
FIG. 4 is a cross-section, schematic view of a coated loop member of the snare loop, in accordance with an embodiment of the present specification.

FIG. 4 is a cross-section schematic view of the coated loop member 105 of a target object capture and retrieval device, fabricated according to an aspect of the present specification. Referring now to FIGS. 1A, 1B, 2A, 3, and 4, at the core of the coated loop member 105 is a wire 130 of diameter 'd' constructed of a resilient yet durable and conducting material that is amenable to be formed into a desired loop shape. In accordance with an embodiment, the diameter 'd' of the wire 130 ranges from 0.2 to 0.6 millimeters. When the coated loop member 105 is extended (FIGS. 1A, 1B and 2A) from its collapsed or retracted position (FIG. 3) within the tubular member or sheath 115, it automatically expands to retain its desired loop shaped configuration, thereby providing an opening to the attached mesh or net 110. Similarly, upon retraction into the tubular member or sheath 115, the coated loop member 105 contracts along with the attached mesh or net 110 and is compacted within the sheath lumen 120. In various embodiments, the wire 130 is made from braided steel, metallic shape memory alloys such as Nitinol, or any other suitable material that is flexible, a conductor of heat and electricity and at the same time sufficiently resilient to maintain its desired loop shape when deployed.

Figure 2C:
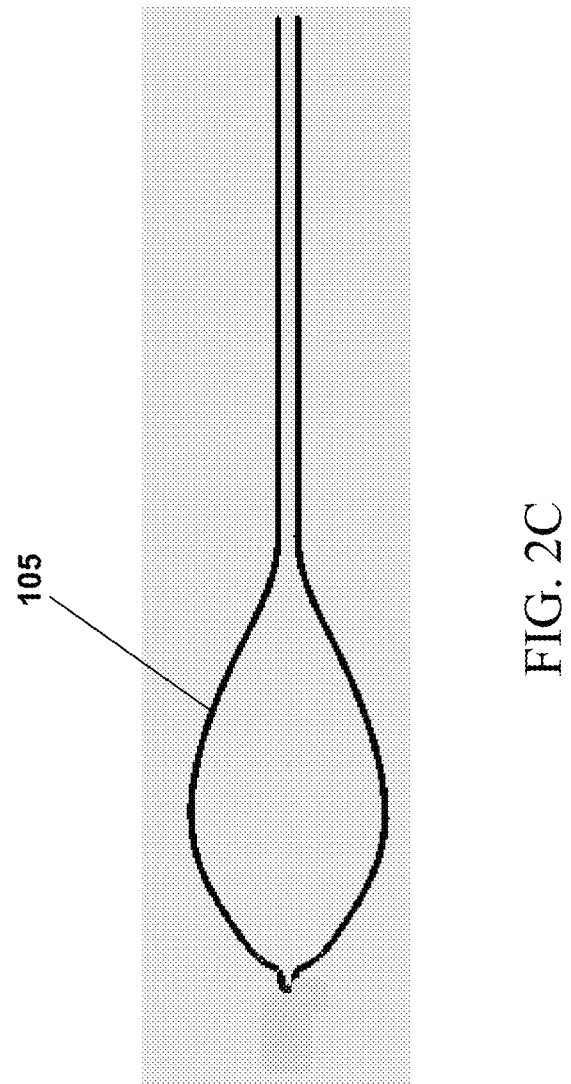
FIG. 2C is a top perspective view showing the snare loop, with mesh removed, in a tear-drop configuration, in accordance with an embodiment of the present specification.

In one embodiment, the desired expanded shape of the wire 130, and therefore of the coated loop member 105, is a tear-drop shape (as shown in FIG. 2C illustrating the coated loop member 105 with its mesh/net removed), while in alternate embodiments the desired expanded shape is oval (FIGS. 1A, 1B), circular, square, rectangular, quadrilateral, polygonal, or any other suitable shape that would be advantageously evident to persons of ordinary skill in the art. Referring to FIG. 1A, in one embodiment described with respect to the oval or tear-drop shape, the loop has a first dimension $L_1$ along a longitudinal axis 150 passing through a reference center 155 of the loop and a second dimension $L_2$ along another axis 165 substantially perpendicular to the longitudinal axis 150 and also passing through the reference center 155 of the loop. In various embodiments, the first dimension $L_1$ is greater than the second dimension L2. In some embodiments, the first dimension $L_1$ is equal to the second dimension L2. In still other embodiments, the first dimension $L_1$ is less than the second dimension L2. In accordance with various embodiments, when the desired shape of the wire 130 is tear-drop or oval, the first dimension L1 ranges from 30 to 70 millimeters and the second dimension $L_2$ ranges from 15 to 40 millimeters.

Referring back to FIG. 4, in accordance with an aspect of the present specification, the wire 130 is coated by, or enveloped into, a layer 135 having a thickness 't' and composed of a polymeric material that, in one embodiment, functions as a 'self-bonding adhesive'. As used herein, the term 'self-bonding adhesive' is defined to mean a material that can be altered (or partially melted), as by the application of heat or a solvent, to become sufficiently tacky or sticky that it will form a secure bond with another polymeric material and/or metal upon cooling. The 'self-bonding adhesive' will bond the mesh to the loop in the area of contact between the two and provide a solid connection once the adhesive has cooled. For purposes of the present specification, tacky is defined as having a sticky quality or being partially wet or not being fully dry and increased tackiness is defined as having an increased sticky quality or being partially wet or not being fully dry, thereby increasing its stickiness quality. Polymeric materials, when heated to a temperature less than their decomposition or ignition temperatures, become thermoplastic with sufficient tackiness, or adhesive properties, to bond to a similar surface or a dissimilar surface, such as metal. Examples of polymeric materials comprise polyolefins, PET (Polyethylene Terephthalate), polyurethanes, polynorbornenes, polyethers, polyacrylates, polyamides (Polyether block amide also referred to as Pebax), polysiloxanes, polyether amides, polyether esters, trans-polyisoprenes, polymethyl methacrylates (PMMA), cross-linked trans-polyoctylenes, cross-linked polyethylenes, cross-linked polyisoprenes, cross-linked polycyclooctenes, inorganic-organic hybrid polymers, co-polymer blends with polyethylene and Kraton®, styrene-butadiene co-polymers, urethane-butadiene co-polymers, polycaprolactone or oligo caprolactone co-polymers, polylactic acid (PLLA) or polylactide (PL/DLA) co-polymers, PLLA-polyglycolic acid (PGA) co-polymers, and photo-crosslinkable polymers.

In one embodiment, the polymeric material of the layer 135 is Nylon or Pebax. In one embodiment, the layer 135 is formed by coating the wire 130 with polymeric material, such as Pebax, using conventional methods such as extrusion, over-molding or dipping. In another embodiment, the layer 135 is a hollow tube of polymeric material, such as Pebax, into which the wire 130 is inserted such that the tube envelopes or covers the wire 130 like a sheath. In some embodiments, the layer 135 in the form of a hollow tube has an internal diameter ranging between 0.3 mm and 1.0 mm and an outer diameter ranging between 0.5 mm and 1.50 mm. In various embodiments, the layer 135 in the form of coating or hollow tube of polymeric material, such as Pebax, has a thickness 't' ranging from 0.05 mm to 0.6 mm.

Figure 5A:
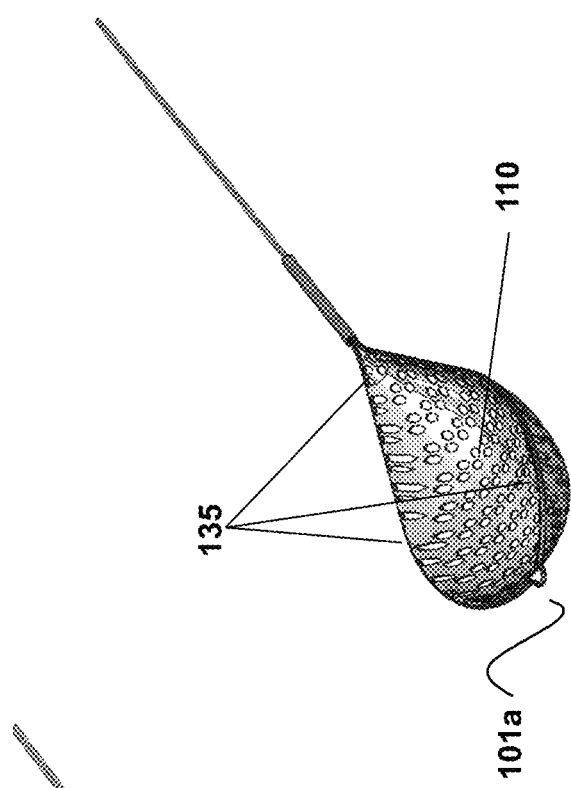
FIG. 5A illustrates the coated loop member of the snare loop, in accordance with some embodiments of the present specification.
Figure 5B:
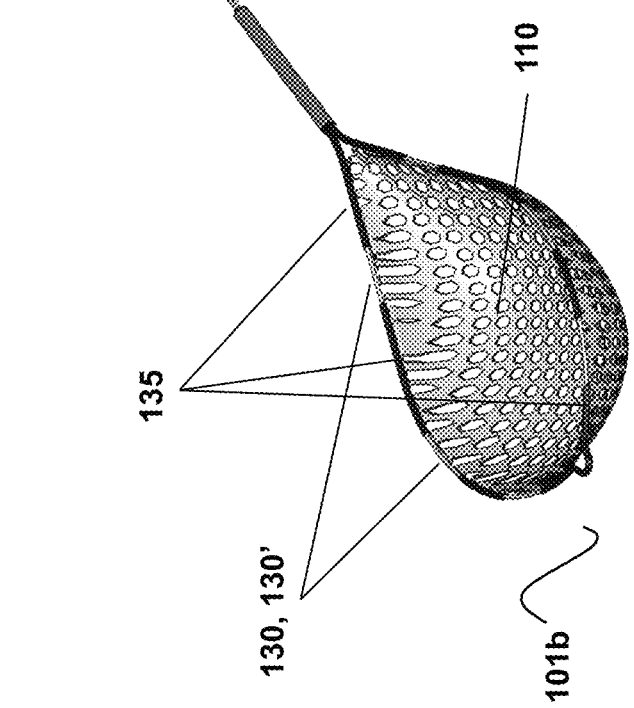
FIG. 5B illustrates the coated loop member of the snare loop, in accordance with another embodiment of the present specification.

FIG. 5A shows an embodiment of the snare loop 101a wherein the layer 135 (in the form of coating or hollow tube) continuously envelops or covers the wire 130. In an alternate embodiment, shown as the snare loop 101b in FIG. 5B, layer 135 is segmented into a plurality of segments such that a plurality of portions 130' of the wire 130 remain bare or without the coating or hollow tube (layer 135). This discontinuous or segmented layer 135 provides the mesh 110 more flexibility to deform when the snare loop 101 is being extended or retracted. In accordance with an aspect, the layer 135 (in the form of coating or hollow tube) and/or the mesh 110 has a bright color such as, but not limited to, blue, green, or red. The bright color of the layer 135 and/or mesh 110 enables improved visibility of the loop and the loop boundaries while the loop 101 is in fluidic communication with bodily fluids, such as during an endoscopic procedure. In various embodiments, color is added to the layer 135 and/or mesh 110 of the snare loop 101a or 101b using masterbatch mixing, pigment blending with or without preliminary compounding, liquid colorant addition, or decoration procedures. In an embodiment, using masterbatch mixing, a polyamide having a viscosity similar to the viscosity of the base material (for example, Pebax) is compounded with the base material. In various embodiments, the rate of incorporation of the polyamide coloring is between 0.3% and 3%. In various embodiments, methods for decorating the layer 135 and/or mesh 110 with the color include laser printing, hot printing, ink printing, clear coat and lacquers, and in-mold techniques, such as co-molding, insert-molding, and in-mold labeling. In an embodiment, after decoration, the layer 135 and/or mesh 110 can be thermoformed and stamped for snare loop assembly.

In accordance with various aspects, the bright color of the layer 135 and/or the mesh 110 is such that when the snare loop 101a or 101b is exposed to light having wavelengths in a first range of 400 to 750 nm (full visible spectrum), it reflects light having a wavelength in a second range. In another embodiment, the snare loop may be exposed to light having wavelengths emitted by conventional illuminators or LEDs used in endoscope devices. In an embodiment, the snare loop is exposed to light from an endoscopic light source, such as a fiber optic light or LED that emits wavelengths ranging from 400 to 750 nm or emits wavelengths in a sub-portion thereof. In another embodiment, the snare loop is exposed to light from an endoscopic light source, such as a fiber optic light or LED that emits wavelengths ranging from 400 to 750 nm with an increased emission at or around blue (450 nm) or green (550 nm).

Figure 6:
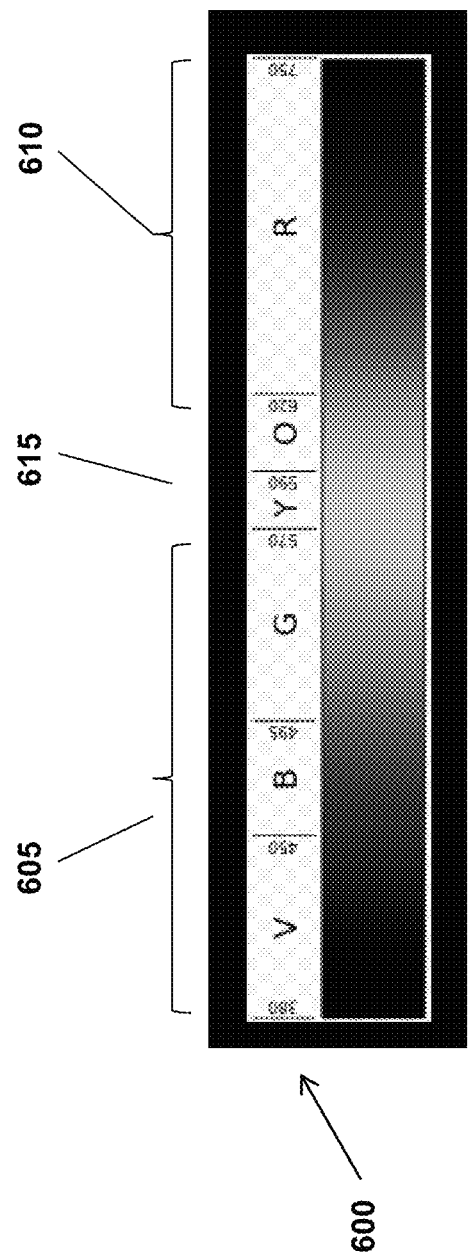
FIG. 6 illustrates a wavelength spectrum of visible light of wavelength ranges that are emitted by the scopes and reflected by the snare loop, in accordance with an embodiment of the present specification.

In one embodiment, the second range is 380 to 750 nm. In another embodiment, the snare loop reflects light having a wavelength in second ranges 605, 610; however, excluding (and thus absorbing) a third range 615 as illustrated in the visible light spectrum 600 of FIG. 6. Therefore, in another embodiment, the second ranges 605, 610 corresponds to a wavelength in a range of 380 to 570 nm and a range of 620 to 750 nm, respectively, while the third range 615 corresponds to a wavelength in a range of 571 to 619 nm, which is not reflected. It should be appreciated that the layer 135 and/or mesh 110 that reflect wavelengths in the second ranges 605, 610 are readily viewable and identifiable even when submerged in or smeared with bodily fluids during an endoscopic procedure.

Conventional snare loops that may be made from non-coated or bare metallic materials that appear silvery or gray in color since metals reflect almost an entire wavelength spectrum of visible light impinging on them. All wavelengths of visible light are absorbed by metals because of the continuously available empty electron states, which permit electron transitions. Most of the absorbed radiation is reemitted from the surface of metals in the form of visible light which appears as reflected light. Similarly, conventional meshes are also whitish gray in color. Since conventional snare loops and meshes typically appear silvery, whitish or gray their visibility is impaired particularly when in fluidic communication with bodily fluids. In contrast to previous designs, the snare loop and/or mesh of the present specification reflect specific wavelength ranges, such as those corresponding to the second ranges 605, 610, but not all wavelengths of the visible spectrum 600 (as reflected by metals). Accordingly, the snare loop is comprised of materials that reflect all wavelengths of the visible spectrum 600, with the exception of wavelengths in a range of 571 to 619 nm.

Figure 7A:
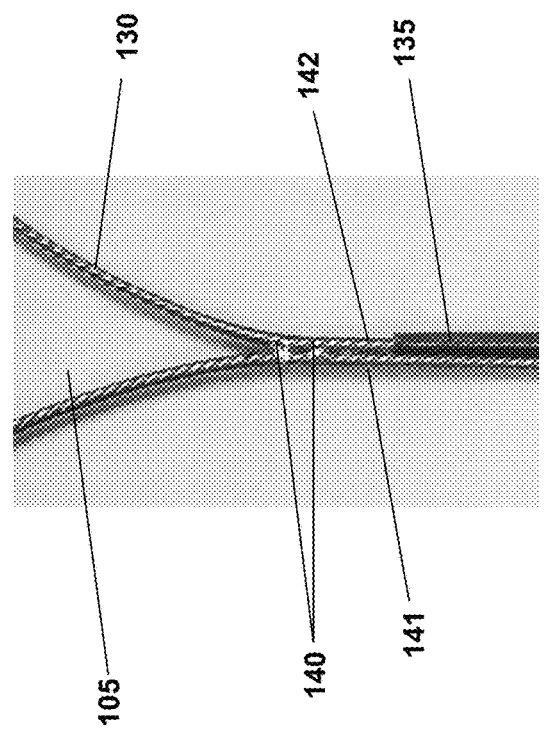
FIG. 7A represents a planar view of a loop member comprising a fastener, bind or clasp, such as at least one weld, at a proximal end of the loop in accordance with an embodiment.
Figure 7C:
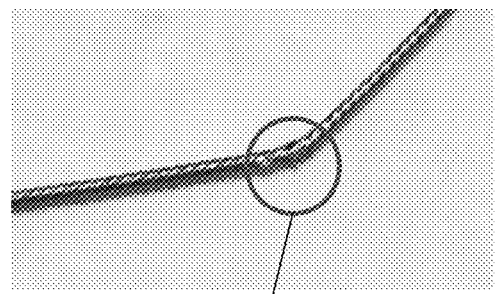
FIG. 7C shows the fastener, such as a weld, cut such that it results in a smooth cut surface.
Figure 7B:
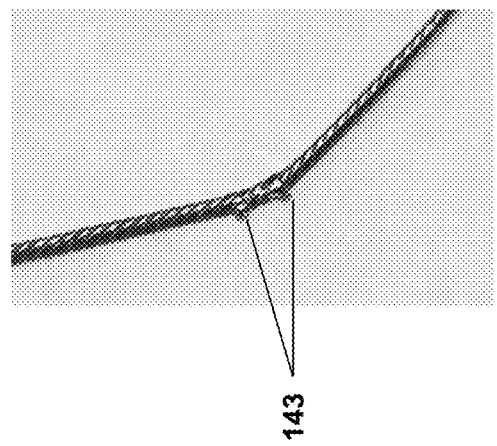
FIG. 7B shows the fastener, such as a weld, having a roughly cut and thus, corrugated or jagged cut surface.

During a process of manufacturing or assembling the snare loop 101 of the present specification, in one embodiment, the wire 130 is first bent or folded into a desired loop shape and thereafter coated or enveloped with the layer 135. In an alternate embodiment, however, the wire 130 is first coated or enveloped with the layer 135 and thereafter bent or folded into a desired loop shape. In some embodiments, the wire 130 which is already bent or folded into the desired loop shape comprises a fastener, bind or clasp 140 at the proximal end of the loop 105, as shown in FIG. 7A. In various embodiments, the fastener, bind or clasp 140 includes at least one weld, hypo tube, at least one clip or any other fixture to hold together the proximal arms 141, 142 resulting from bending of the wire 130 into the loop 105. However, the fastener, bind or clasp 140 interferes in embodiments where the wire 130 needs to be enveloped within a hollow tube 135. Therefore, in one embodiment, the fastener 140, such as at least one weld, is cut without damaging the wire 130 while also maintaining a smooth area or surface at the cut. A fastener or bind, such as a weld, improperly or roughly cut, has corrugated or jagged surface 143, as shown in FIG. 7B, while a properly cut fastener or bind, such as the weld, results in a smooth surface 143' as shown in FIG. 7C. In various embodiments, the wire 130 and/or the internal channel of the hollow tube 135 may be coated with a dry lubricant to reduce friction during the process of sheathing the wire 130 within the hollow tube 135. Non-limiting examples of dry lubricants include PTFE (polytetrafluoroethylene) powder, McLube, Silicon oil, etc. In some embodiments, however, the wire 130 is bent or folded into the desired loop shape without a weld. In such embodiments, sheathing the wire 130 within the hollow tube 135 is easily accomplished.

Hereinafter referring simultaneously to FIGS. 1A, 1B, 2A, 3, 4, 5A, and 5B, along with FIGS. 7A, 7B, 7C and 8-12, in accordance with an embodiment of the present specification, to attach the mesh or net 110 to the coated loop member 105, the mesh or net 110 is placed and held over the coated loop member 105 and the wire 130 is heated. The shape of the mesh 110 is approximated to the shape of the coated loop member 105. Also, the size of the mesh 110 is chosen such that portions of the mesh 110 extend beyond the circumference of the underlying coated loop member 105 along the edges of mesh 110. In one embodiment, the mesh 110 has an intentional slack while being placed over the coated loop member 105. The slack results in the formation of a pouch 145 preferably at the center 155 of the coated loop member 105 after the mesh 110 is attached or connected thereto.

Figure 8:
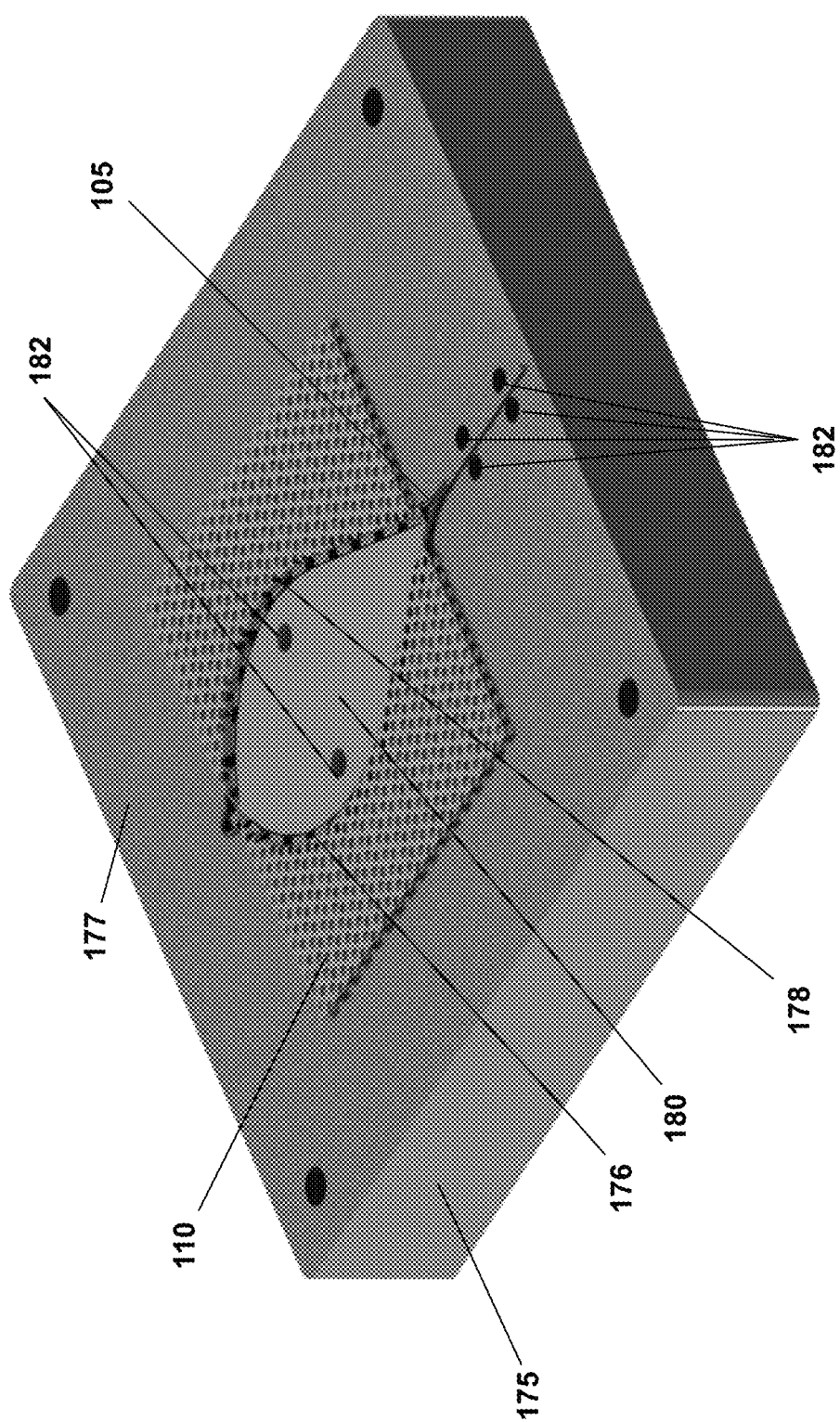
FIG. 8 is a perspective view of a fixture used to attach, bond or connect the mesh to the coated loop member, in an embodiment.

FIG. 8 shows an embodiment of a base fixture 175 that is used to attach the mesh 110 to the coated loop member 105. The base fixture 175 comprises a loop holding area 176, on the upper surface 177 that approximates the shape of the coated loop member 105. The loop holding area 176, in one embodiment, comprises a plurality of magnets 178 that firmly hold the coated loop member 105 in place once the coated loop member 105 is placed over the loop holding area 176. The loop holding area 176 defines a hollow portion there between and formed within the base fixture 175. The hollow portion is configured to receive a pouch form fixture 180 therein.

For assembling, the coated loop member 105 is placed over the loop holding area 176 so that the coated loop member 105 is firmly held by the plurality of magnets 178. The plurality of magnets 178, in one embodiment, are embedded within the base fixture 175 to lie approximately along the circumference or boundary defined by the loop holding area 176. Next, the mesh 110 is placed over the held coated loop member 105. At this point, the mesh 110 covers the coated loop member 105 such that portions of the mesh 110 along its edges extend beyond the circumference of the underlying coated loop member 105. The pouch form fixture 180 is then placed over the portion of the mesh 110 lying above the hollow portion thereby causing, pressing or forcing the mesh 110 into the hollow portion. This pressing of the mesh 110 to fill the hollow portion results in the formation of the pouch 145 (shown in FIG. 1B). In accordance with an aspect, the mesh 110 is held in place by at least the weight of the pouch form fixture 180. A plurality of guide pin holes 182 allow corresponding guide pins to be inserted therein to hold and/or keep the mesh 110, loop 105 and pouch form fixture 180 together in alignment.

Figure 9:
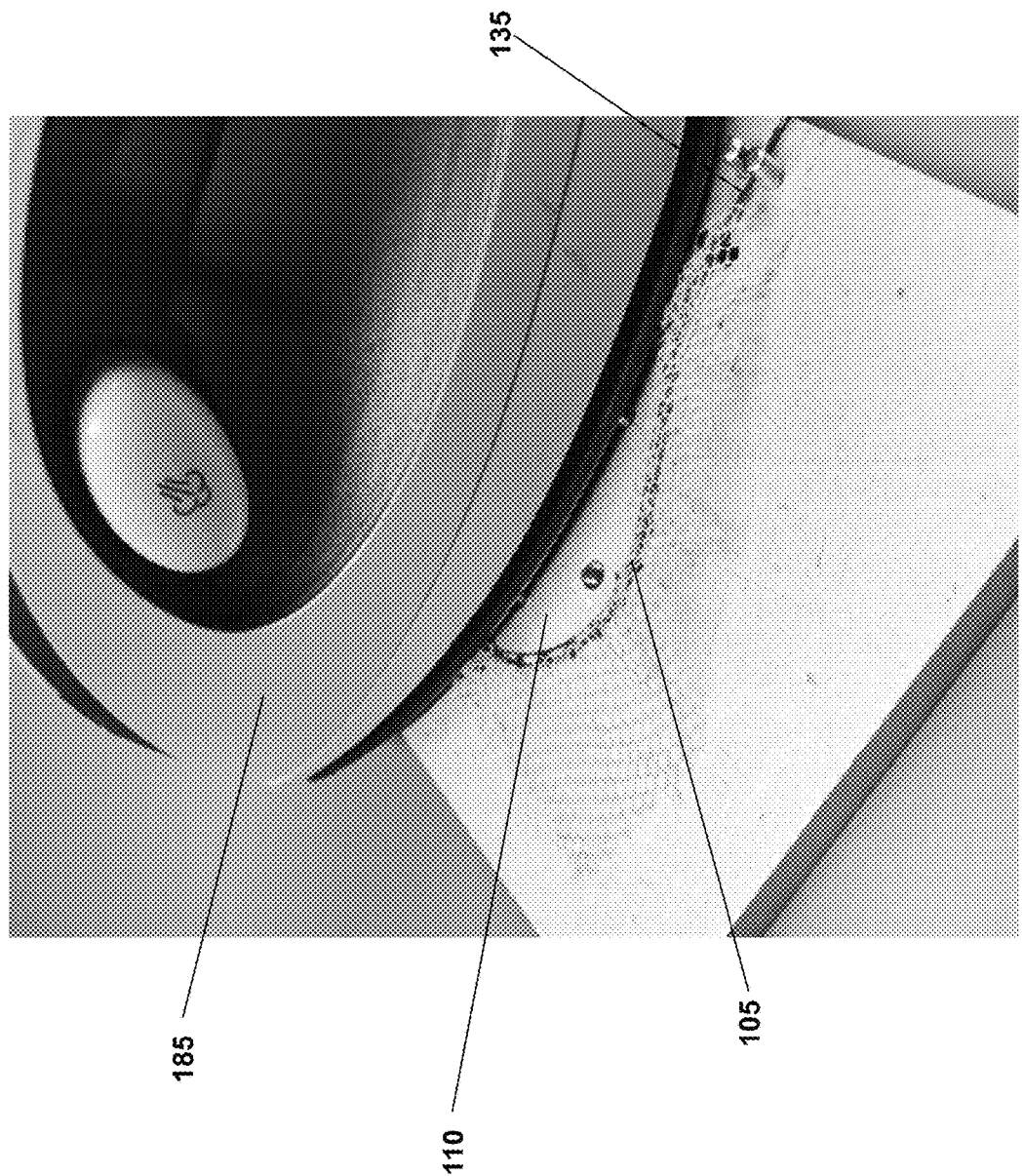
FIG. 9 illustrates a thermal bonding mechanism wherein the mesh is bonded to the coated loop member.

To attach or connect the mesh 110 to the coated loop member 105, the wire 130 is heated to an appropriate temperature, causing the layer 135 of polymeric material, such as Nylon or Pebax, to partially melt, soften and become sufficiently tacky or sticky without burning or decomposing. The appropriate temperature depends at least on the specific polymeric material being used. In one embodiment, heat is transferred to the layer 135 by electrically heating the wire 130 using an external electrical circuit/source. In an alternate embodiment, heat is transferred to the layer 135 by subjecting the coated loop member 105 to a blast of hot air while the overlying mesh 110 is held firmly thereupon. In various embodiments, the hot air has a temperature within a range of 120 to 180° C. or within a range of the melting temperature of the bonding material. In some embodiments, heating is achieved within an oven. In an embodiment, the oven is pre-heated to a specific temperature before placing in it the stated wire and mesh apparatus. In still another embodiment, as shown in FIG. 9, heat is transferred to the layer 135 by hot ironing, thermal pressing or thermal welding the mesh 110 along its edges overlying the circumference of the coated loop member 105 using a hot iron, thermal press 185 (or any other heat source evident to persons of ordinary skill in the art). As a result, the plurality of polymeric strands (such as Nylon, or PET strands, for example) of the mesh 110 are bonded to the loop wire by the tacky or sticky layer 135, thus forming a secure bond upon cooling.

Figure 10:
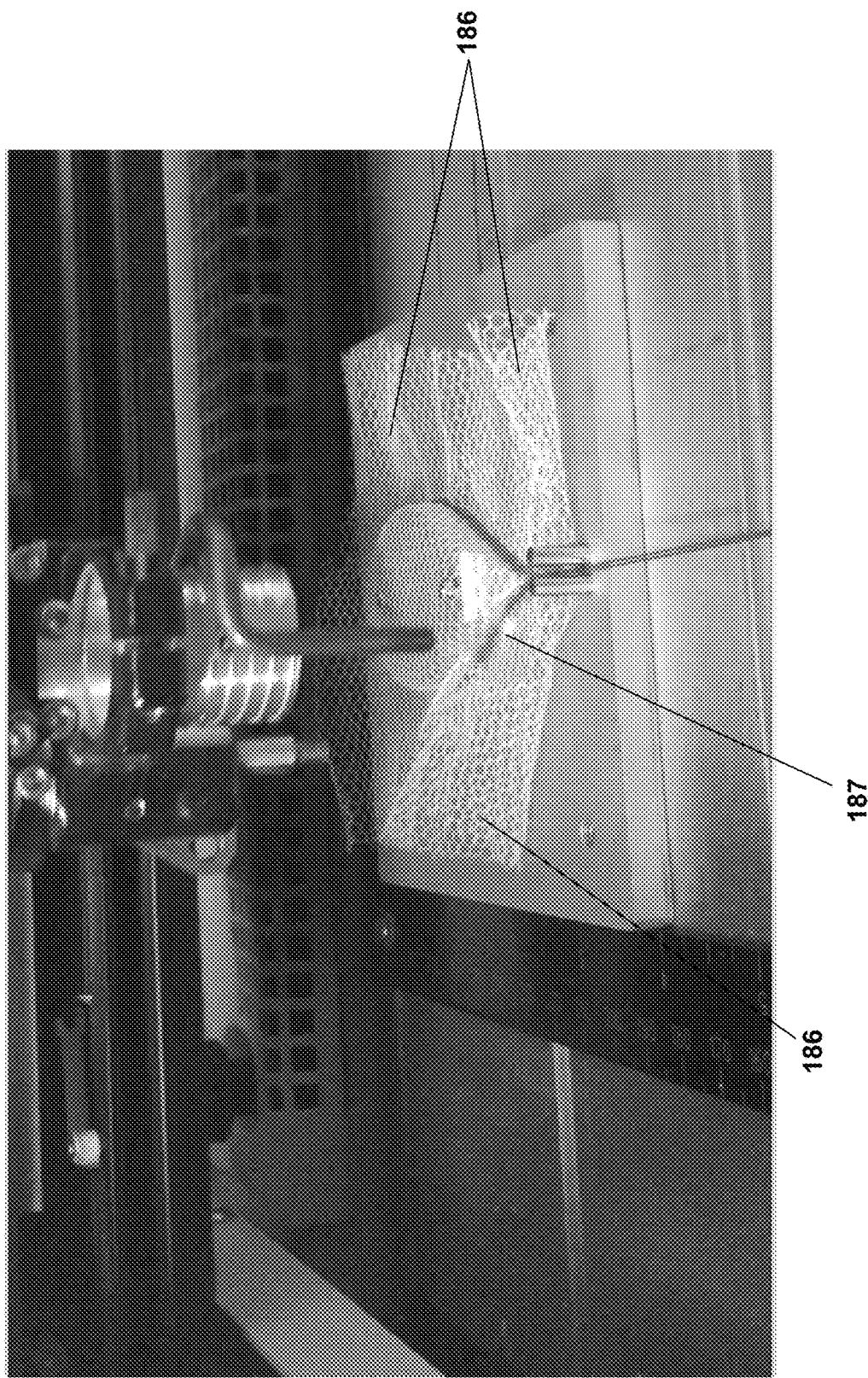
FIG. 10 illustrates the use of a laser beam, in accordance with an embodiment, to cut extending portions of the mesh bonded to the coated loop member.
Figure 11:
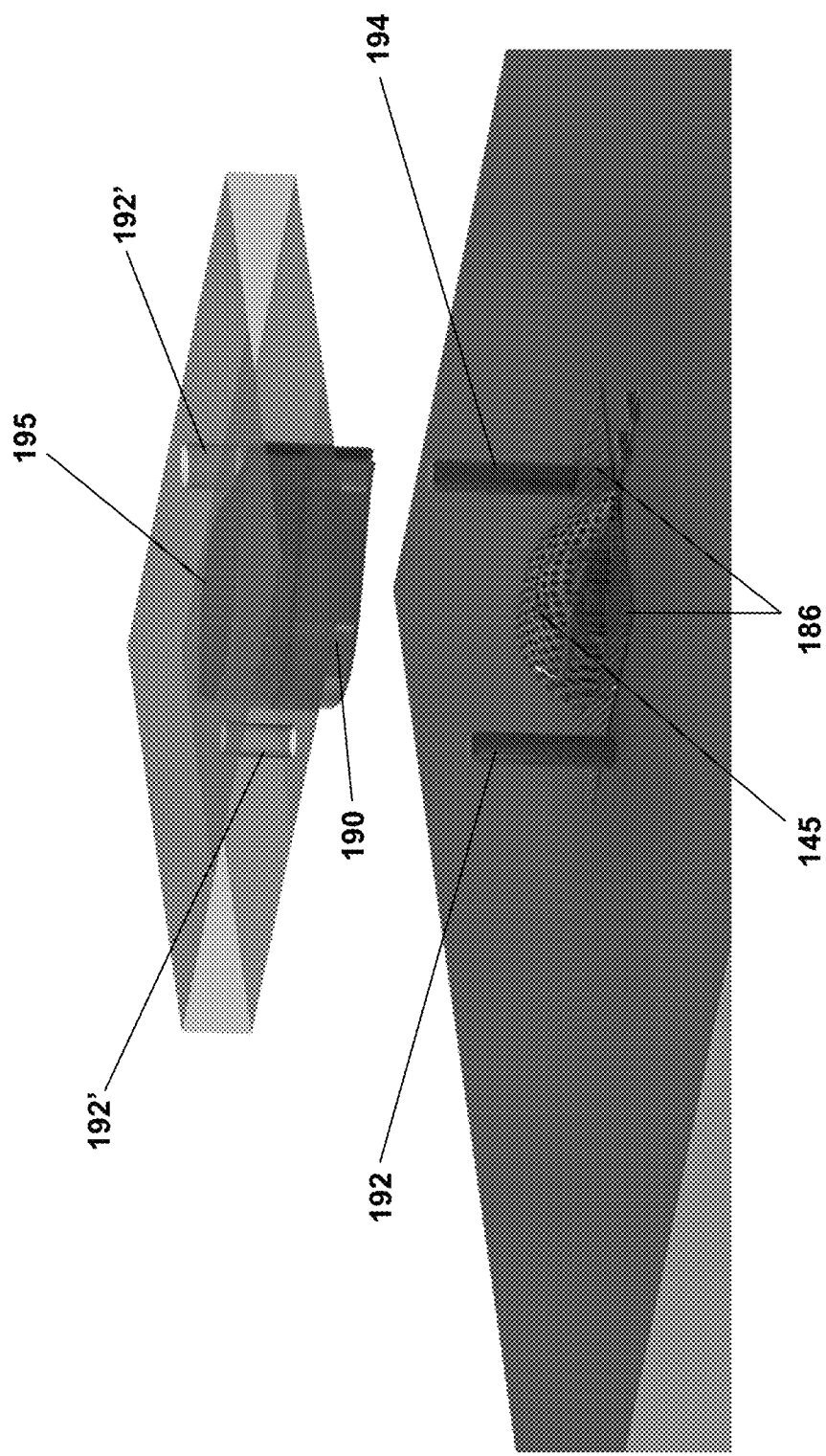
FIG. 11 is a perspective view of a mesh cutting die, used to cut extending portions of the mesh bonded to the coated loop member.

Upon secure bonding of the mesh 110 with the layer 135 (and therefore the coated loop member 105), as shown in FIG. 10, portions 186 of the mesh 110 extending beyond the circumference of the coated loop member 105 are cut or trimmed to remove loose ends or portions 186 (also referred to as 'extending portions'). In one embodiment, as shown in FIG. 10 a laser beam 187 is used to cut or trim the extending portions 186. In an alternate embodiment, as shown in FIG. 11, a mesh cutting die 190 is used. As shown, the attached, bonded or fused mesh 110 and coated loop member 105 assembly (hereinafter also referred to as 'bonded assembly') is placed and aligned between the guiding or alignment pins 192 and 194. The cutting die 190 approximates the shape of the loop member 105 and also has a hollow portion 195 that encompasses the formed pouch 145 when the die 190 is pressed over the 'bonded assembly'. Forcing or force pressing the die 190 over the 'bonded assembly' results in cutting or trimming of the extending portions 186. Mating holes 192' receive the alignment pins 192 when the cutting die 190 is pressed over the 'bonded assembly' to enable proper alignment of the die 190 with reference to the 'bonded assembly', thereby precisely cutting or trimming of the extending portions 186. In still further embodiments, ultrasonic welding is employed to cut or trim the extending portion 186. Heat is generated via ultrasonic welding, thereby melting regions of the mesh and cutting them.

Figure 12:
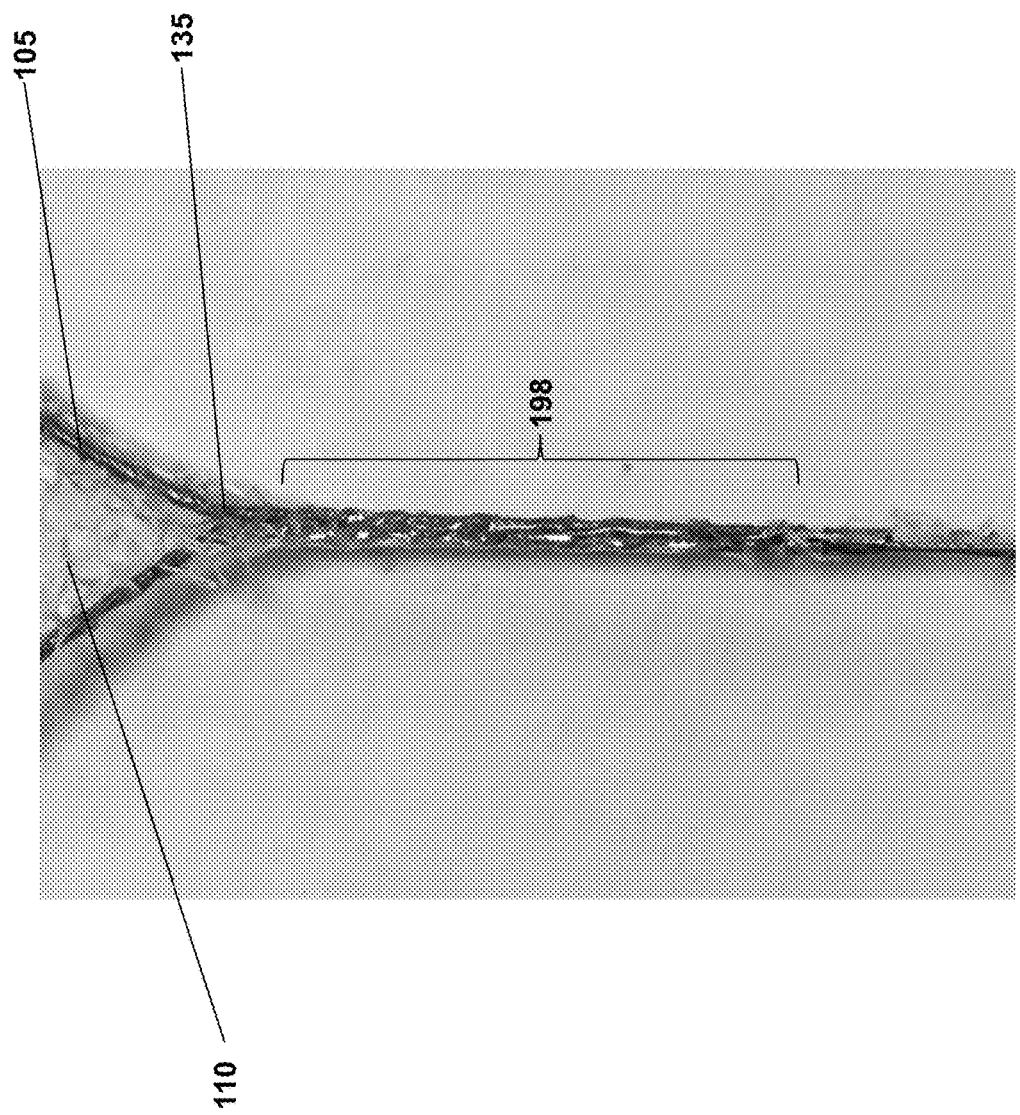
FIG. 12 illustrates a portion of the mesh bonded along a proximal length of the coated loop member, forming a shrink tube that reinforces the proximal end of the coated loop member; and, FIG. 13 is a flow chart illustrating exemplary steps of attaching/connecting a mesh/net to a coated loop member, in accordance with an embodiment of the present specification.

As shown in FIG. 12, in accordance with an embodiment, portions of the mesh 110 extending over a proximal length 198 of the loop 105 are fused or bonded with a corresponding portion of the layer 135 along the proximal length 198. Post cutting or trimming of the extended portions 186 (shown in FIGS. 10 and 11), the proximal length 198 retains the fused portions of the mesh 110 forming a shrink tube thereon, thereby holding together and providing sufficient reinforcement to the proximal arms 141, 142 (visible in FIG. 7A).

In accordance with alternate embodiments of the present specification, the mesh 110 is directly bonded to the wire 130, obviating a need for the layer 135. In such embodiments, the mesh 110 is bonded to the wire 130 using: an adhesive, which is subsequently dried; ultra-violet, laser or thermal welding; heat staking; or, any other method known to persons of ordinary skill in the art. In one embodiment, the mesh 110 is directly glued to the wire 130 (without the need for the layer 135) using an UV (ultra-violet) cure adhesive in a curing process wherein high-intensity ultra-violet light or radiation is used to speed up the curing or drying of the adhesive (by exposing or irradiating the adhesive with ultra-violet radiation). An example of an UV cure adhesive is the Loctite® brand of adhesives sold by Henkel.

In use, the tubular member or sheath 115, having the flexible and extensible coated loop member 105 compacted within, is inserted through a working or service channel of an endoscope to position near a target object, such as a polyp, severed human tissue, foreign object or impacted food bolus within a body lumen. When capture of the target object is about to be performed, the coated loop member 105 is extended out from the tubular member or sheath 115 and, in the process, automatically expands, thereby providing an opening to the attached mesh 110 and therefore to the pouch 145. In one embodiment, when the target object is captured in the mesh 110, the coated loop member 105 is partially retracted to secure the target object within the mesh 110. In another embodiment, once the target object is captured in the mesh 110, the retrieval device and target object are removed from the patient without retracting the coated loop member 105 into the sheath 115. In one embodiment, presence of the pouch 145 further aids in securely retaining the target object.

Figure 13:
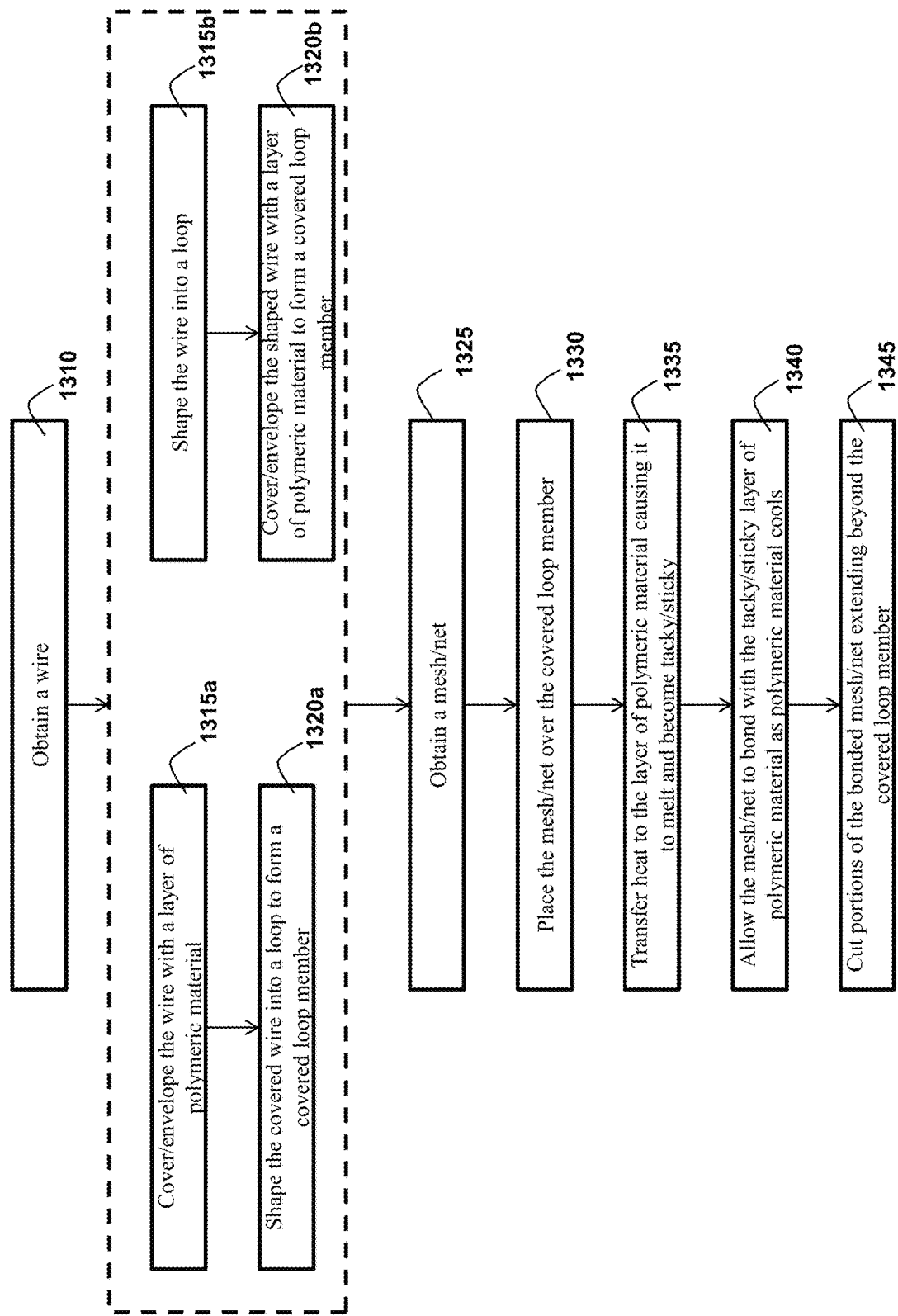

FIG. 13 is a flow chart illustrating exemplary steps of a method of forming a coated loop member and attaching, bonding or connecting a mesh or net to the coated loop member, in accordance with various embodiments of the present specification. At step 1310, a wire is obtained. The wire has a diameter 'd' and is of braided steel, stainless steel, Nitinol or any other shape memory alloy known to persons of ordinary skill in the art. In one embodiment, at step 1315a, the wire is coated with or enveloped in a layer of polymeric material, such as but not limited to Nylon or Pebax, of thickness 't'. The layer may be formed by coating the wire with the polymeric material or inserting the wire in a hollow tube of polymeric material. The wire, coated or enveloped with the layer of polymeric material, is then manipulated, such as by bending or folding, into a loop of desired shape and size to form a coated loop member, at step 1320a. In another embodiment, at step 1315b, the wire is first manipulated, such as by bending or folding, into a loop of desired shape and size. Thereafter, at step 1320b, the shaped loop wire is coated with or enveloped in a layer of polymeric material to form a coated loop member.

In some embodiments, the wire which is first bent or folded into the desired loop shape, at step 1315b, comprises a fastener, bind or clasp at a proximal end of the loop to hold together the proximal arms resulting from bending of the wire. In various embodiments, the fastener, bind or clasp includes at least one weld, hypo tube, at least one clip or any other fixture evident to persons of ordinary skill in the art. In such embodiments, the fastener, such as at least one weld, is first cut or removed prior to the step 1320b of coating or enveloping the wire with a layer of polymeric material (such as a hollow tube, in one embodiment) to form the coated loop member.

In various embodiments, the desired shape of the loop is oval, circular, tear-drop, square, rectangular, quadrilateral or polygonal. In one embodiment, the loop has a first dimension along a longitudinal axis passing through a center of the coated loop member and a second dimension along another axis perpendicular to the longitudinal axis and also passing through the center of the coated loop member. In various embodiments, the first dimension is longer than the second dimension. In some embodiments, the first dimension is equal to the second dimension. In still other embodiments, the first dimension is less than the second dimension. It should be appreciated that the coated loop member is formed either using step 1315*a* followed by 1320*a* or alternatively using step 1315*b* followed by 1320*b*.

Next, at step 1325, a mesh, web or net of polymeric material, such as but not limited to Nylon, PET is obtained. The mesh is of a shape approximating the shape of the coated loop member and is of a size that is somewhat larger than the size of the coated loop member. At step 1330, the coated loop member is placed on a base fixture that has a plurality of magnets to hold the coated loop member in place. Thereafter, the mesh or net is placed and held over the coated loop member such that portions of the mesh along its edges extend beyond the circumference of the coated loop member. In some embodiments, the mesh partially covers a circumference of the loop member. In other embodiments, the mesh completely covers a circumference of the loop member. In one embodiment, a portion of the mesh, covering the center of the coated loop member, is pressed or forced to lie within a hollow, defined within the base fixture, using a pouch forming fixture (so that the mesh is held in place by at least the weight of the pouch form fixture). This causes the mesh to have an intentional slack while being placed over the coated loop member. The slack results in the formation of a pouch at the center of the coated loop member after the mesh is connected to the coated loop member.

Now, at step 1335, heat is transferred to the layer of polymeric material. In one embodiment, the wire of the coated loop member is heated to an appropriate temperature causing the layer of polymeric material to partially melt, soften and become sufficiently tacky, slightly sticky, or partially wet without getting burnt or decomposing. Heat is transferred to the layer of polymeric material using methods such as, but not limited to, electrically heating the underlying wire using an external electrical circuit or source such as an oven, exposing the coated loop member to hot air blast (the mesh placed over the loop is firmly held in place while the hot air blast is blown over both), applying a hot iron, thermal press over the mesh along its boundary overlying the circumference of the coated loop member, or any other method that would be advantageously evident to persons of ordinary skill in the art. As a result, at step 1340, a plurality of strands of the mesh, lying over the surface of the circumference of the coated loop member, fuse with or get glued to the tacky or sticky layer and securely bond with the coated loop member upon cooling. Finally, at step 1345, portions of the bonded mesh extending beyond the circumference of the coated loop member are cut or trimmed using a laser beam, ultrasonic welding or a mesh cutting die. This ensures that there are no loose ends or strands extending beyond the coated loop member as this might cause the mesh to tear and/or damage surrounding tissue when in use during endoscopic procedures.

The above examples are merely illustrative of the many applications of the methods and systems of present specification. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:
1. A retrieval device comprising:
a flexible wire loop lying in a plane, wherein a plane of bisection bisects a wire of the wire loop into a first side and a second side, wherein the plane of bisection is parallel to the plane in which the wire loop is lying;
a bonding material layered over and enveloping said wire loop, wherein the bonding material includes a first section on the first side of the wire and a second section on the second side of the wire;
a mesh bonded to said bonding material and configured to form a net having an opening circumscribed by said wire loop, wherein said mesh has been fixedly bonded to said bonding material through a process of heating said bonding material to a tacky state, placing an outer edge of said mesh over said bonding material, and allowing said bonding material to cool, wherein the mesh includes a plurality of strands surrounding a plurality of pores, portions of the plurality of strands being coupled to the first section of the bonding material, along an outer periphery of the mesh, wherein the plurality of strands are only coupled to the first section; and
a tubular sheath comprising an elongate body, a proximal end, a distal end, and a lumen within, wherein said flexible wire loop with bonded mesh is adapted to be retractable into said lumen and adapted to be extendable out of said lumen through an opening at said distal end of said tubular sheath by manipulation of a link member positioned at said proximal end of said tubular sheath, and wherein at least one of said loop and said mesh comprise a color such then when exposed to light in a first wavelength range, reflects light having a wavelength range of 400 nm to 570 nm and 620 nm to 750 nm and absorbs light having a wavelength range of 571 nm to 619 nm.

2. The device of claim 1, wherein said mesh has a porosity ranging between 15 and 40 pores per cm$^2$.

3. The device of claim 1, wherein said pores have a hexagonal, circular, triangular, square, rectangular, pentagonal or multi-sided polygonal shape.

4. A retrieval device comprising:
a snare loop, including:
a central opening,
a loop member surrounding the central opening and lying in a plane, wherein a plane of bisection bisects a wire of the loop member into a first side and a second side, wherein the plane of bisection is parallel to the plane in which the wire loop is lying, and
a layer of material that overlies the loop member, wherein the layer of material includes a first section on the first side of the wire and a second section on the second side of the wire;
a mesh extending across the central opening of the snare loop, wherein said mesh defines a plurality of pores and has a porosity ranging between 15 and 40 pores per cm$^2$, and wherein each pore is defined by a plurality of sides each consisting of a strand of a plurality of strands of the mesh,
wherein each of the plurality of strands includes a plurality of openings, wherein each of the plurality of openings is smaller than each of the plurality of pores;
wherein portions of the plurality of strands are coupled to, and fixed and immovable relative to, the layer of material along an outer periphery of the mesh, wherein the portions of the plurality of strands are only coupled to the first section;
a sheath, including:
a lumen,
a proximal end,
a distal end, and a distal opening, wherein the lumen extends between the proximal end and the distal end, and wherein the lumen is in communication with the distal opening; and a drive element extending through the lumen of the sheath to the snare loop, wherein movement of the drive element within the lumen of the sheath is configured to:

move at least a portion of the snare loop, and at least a portion of the mesh, distally out of the distal opening of the sheath, and move at least the portion of the snare loop, and at least the portion of the mesh, proximally into the distal opening of the sheath, wherein the portions of the plurality of strands remain stationary relative to the layer of material as the snare loop and the mesh move through the distal opening of the sheath.

5. The retrieval device of claim 4, wherein each of the plurality of pores is hexagonal.

6. The retrieval device of claim 4, wherein the layer of material is colored such that when the layer of material is exposed to light having a wavelength in a first range, the layer of material reflects light having a wavelength in a second range different from the first range.

7. The retrieval device of claim 6, wherein the second range is a subset of the first range.

8. The retrieval device of claim 6, wherein the reflected light has a wavelength of between 380 and 570 nm.

9. The retrieval device of claim 6, wherein the reflected light has a wavelength of between 620 to 750 nm.

10. The retrieval device of claim 4, wherein each of the plurality of pores is polygonal.

11. The retrieval device of claim 4, wherein a color of the layer of material is blue.

12. A retrieval device comprising:

a flexible wire loop lying in a plane, wherein a plane of bisection bisects a wire of the wire loop into a first side and a second side, wherein the plane of bisection is parallel to the plane in which the wire loop is lying;

a layer of material enveloping the wire loop, wherein the layer of material includes a first section on the first side of the wire and a second section on the second side of the wire;

a mesh bonded to the layer of material and configured to form a net having an opening circumscribed by said wire loop, wherein the mesh includes a plurality of strands and a plurality of pores between the plurality of strands, wherein portions of the plurality of strands are coupled to the layer of material, wherein the portions of the plurality of strands are positioned along an outer periphery of the mesh and include one or more terminal ends, and wherein the one or more terminal ends are directly and immovably coupled to, and enveloped by, the layer of material, wherein the one or more terminal ends are only coupled to the first section; and a tubular sheath comprising an elongate body, a proximal end, a distal end, and a lumen within, wherein said flexible wire loop with bonded mesh is adapted to be retractable into said lumen and adapted to be extendable out of said lumen through an opening at said distal end of said tubular sheath, by manipulation of a link member positioned at said proximal end of said tubular sheath, and wherein at least one of said flexible wire loop and said mesh comprise a color such then when exposed to light in a first wavelength range, reflects light having a wavelength range of 400 nm to 570 nm and 620 nm to 750 nm and absorbs light having a wavelength range of 571 nm to 619 nm.

13. The device of claim 12, wherein each pore is defined by a plurality of sides each consisting of a strand of the plurality of strands of the mesh, and wherein each of the plurality of strands includes a plurality of openings, wherein each of the plurality of openings is smaller than each of the plurality of pores.

14. The device of claim 12, wherein the portions of the plurality of strands are coupled to the first section of the layer of material.

15. The device of claim 12, wherein the mesh has a porosity ranging between 15 and 40 pores per $cm^2$.

16. The device of claim 12, wherein the wire loop includes a first proximal arm and a second proximal arm, the device further comprising:

a drive strand extending through the lumen of the tubular sheath to the wire loop, wherein movement of the drive strand within the lumen of the tubular sheath is configured to move the snare loop and the mesh relative to the sheath, and wherein the portions of the plurality of strands that are coupled to the layer of material remain fixed relative to the layer of material during movement of the snare loop and the mesh into and out of the distal opening of the sheath; and a shrink tube configured to secure the first proximal arm to the second proximal arm, wherein the first proximal arm and second proximal arm contact each other within the shrink tube, and wherein the shrink tube comprises portions of the mesh.

17. The device of claim 12, wherein the plurality of pores have a hexagonal, circular, triangular, square, rectangular, pentagonal or multi-sided polygonal shape.

18. The device of claim 12, wherein the portions of the plurality of strands are fused to the layer of material.

19. The device of claim 12, wherein the mesh may be advanced, stretched or elongated by a minimum of 10% to 40% in a machine direction and advanced, stretched or elongated by a minimum of 20% to 70% in a cross machine direction.

* * * * *